United States Patent [19]

Roper

[11] Patent Number: 4,480,133

[45] Date of Patent: Oct. 30, 1984

[54] CHEMICAL PROCESS

[75] Inventor: Jerry M. Roper, Baton Rouge, La.

[73] Assignee: Ethyl Corporation, Richmond, Va.

[21] Appl. No.: 472,196

[22] Filed: Mar. 4, 1983

[51] Int. Cl.³ ............................................. C07C 45/45
[52] U.S. Cl. .................................... 568/362; 568/367; 568/329; 568/322
[58] Field of Search ................. 568/362, 367, 322, 329

[56] References Cited

U.S. PATENT DOCUMENTS 2,560,280  7/1951  Benneville et al. .................. 564/286
4,261,866  4/1981  Barton et al. ........................ 568/307

FOREIGN PATENT DOCUMENTS 1109675  6/1961  Fed. Rep. of Germany ...... 568/367

OTHER PUBLICATIONS

McClure, J. Org. Chem., vol. 27, pp. 2305–2308, (1962).
Hatchard, J.A.C.S., vol. 80, pp. 3640–3642, (1958).

*Primary Examiner*—James H. Reamer
*Attorney, Agent, or Firm*—Donald L. Johnson; John F. Sieberth; W. G. Montgomery

[57] ABSTRACT

Novel 2,4-dihydrocarbylspiro[5.5]undeca-1,4,8-trien-3-one compounds are prepared by reacting an N,N-dihydrocarbyl,2,6-dihydrocarbyl-4-aminomethylphenol with a conjugated diene and an alkyl halide in a liquid solvent medium.

20 Claims, No Drawings

CHEMICAL PROCESS

TECHNICAL FIELD

This invention relates to novel spiroketone compounds, their preparation and uses.

THE INVENTION

The present invention provides novel spiroketone compounds of the general formula:

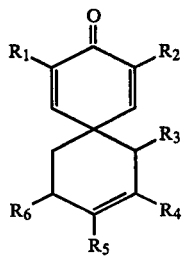

and the structural isomers thereof, wherein $R_1$ and $R_2$ are the same or different and are hydrogen or hydrocarbyl radicals, preferably alkyl, aralkyl, or cycloalkyl radicals having up to at least 40 carbon atoms and $R_3$, $R_4$, $R_5$, and $R_6$ are the same or different and are hydrogen or linear or branched alkyl, aralkyl or cycloalkyl radicals having up to 8 carbon atoms each.

The compounds of this invention are prepared by reacting an N,N-dihydrocarbyl,2,6-dihydrocarbyl-4-aminomethylphenol with an alkyl halide and a conjugated diene in a liquid solvent medium. Thus, one embodiment of the present invention is a novel process for the preparation of 2,4-dihydrocarbylspiro[5.5]undeca-1,4,8-trien-3-one compounds which comprises reacting an N,N-dihydrocarbyl,2,6-dihydrocarbyl-4-aminomethylphenol with a conjugated diene and an alkyl halide in the presence of a liquid solvent.

The process can be illustrated schematically by the following equation. Compounds having the general formula:

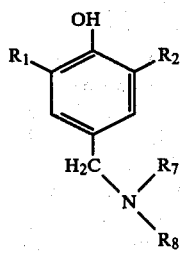
(I)

are reacted with compounds having the general formula:

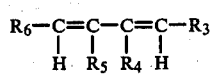
(II)

and an alkyl halide of the general formula:

(III)

in the presence of a liquid solvent to yield 2,4-dihydrocarbylspiro[5.5]undeca-1,4,8-trien-3-one compounds having the structural formula:

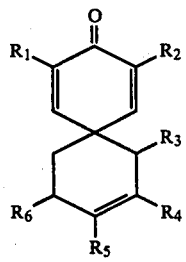

and the structural isomers thereof.

In the structural formulas above, $R_1$ and $R_2$ are the same or different and are hydrogen or hydrocarbyl radicals, preferably alkyl, aralkyl, or cycloalkyl radicals having up to at least 40 carbon atoms and $R_3$, $R_4$, $R_5$ and $R_6$ are the same or different and are hydrogen or linear or branched alkyl, aralkyl, or cycloalkyl radicals having up to 8 carbon atoms each; $R_7$ and $R_8$ are the same or different and are hydrogen or hydrocarbyl radicals, preferably branched or unbranched alkyl, aralkyl, or cycloalkyl radicals having up to at least 20 carbon atoms; $R_9$ is a linear or branched monovalent alkyl radical having up to at least 20 carbon atoms and X is chlorine, bromine or iodine.

Thus, in another embodiment of the present invention, there is provided a process for the preparation of 2,4-dihydrocarbylspiro[5.5]undeca-1,4,8-trien-3-one compounds having the general formula:

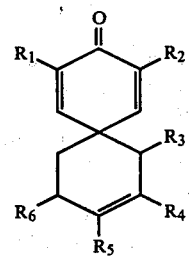

and the structural isomers thereof, which comprises reacting an N,N-dihydrocarbyl,2,6-dihydrocarbyl-4-aminomethylphenol of the general formula:

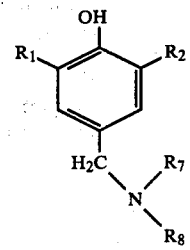
(I)

with a conjugated diene of the general formula:

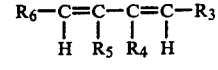
(II)

and an alkyl halide of the formula:

R₉X    (III)

in the presence of a liqud solvent wherein in the structural formulas above, $R_1$ and $R_2$ are the same or different and are hydrogen or hydrocarbyl radicals having up to at least 40 carbon atoms and $R_3$, $R_4$, $R_5$ or $R_6$ are the same or different and are hydrogen or linear or branched alkyl, aralkyl or cycloalkyl radicals having up to 8 carbon aoms each; $R_7$ and $R_8$ are the same or different and are hydrogen or hydrocarbyl radicals having up to at least 20 carbon atoms; $R_9$ is a linear or branched monovalent alkyl radical having up to at least 20 carbon atoms and X is bromine, chlorine or iodine.

Representative examples of radicals described above are secondary radicals such as secondary butyl, secondary amyl, secondary octyl; tertiary radicals such as tertiary butyl, tertiary hexyl and tertiary decyl; alkyl radicals such as methyl, ethyl, propyl, butyl, nonyl, decyl, tetradecyl, hexadecyl, nonadecyl; aralkyl radicals such as methyl phenyl and pentyl phenyl, and cycloalkyl radicals such as cyclopentyl, cyclohexyl and cycloheptyl radicals.

Representative examples of the Group I compounds include:
2,6-di-t-butyl-4-aminomethylphenol;
N-methyl,2,6-di-t-butyl-4-aminomethylphenol;
N,N-dimethyl,2-methyl-4-aminomethylphenol;
N,N-dimethyl,2-ethyl-4-aminomethylphenol;
N,N-dimethyl,2-isopropyl-4-aminomethylphenol;
N,N-dimethyl,2-sec-butyl-4-aminomethylphenol;
N,N-dimethyl,2-butyl-4-aminomethylphenol;
N,N-dimethyl,2-heptyl-4-aminomethylphenol;
N,N-dimethyl,2-octyl-4-aminomethylphenol;
N,N-dimethyl,2,6-dimethyl-4-aminomethylphenol;
N,N-dimethyl,2,6-diethyl-4-aminomethylphenol;
N,N-dimethyl,2-octyl-4-aminomethylphenol;
N,N-dimethyl,2,6-dimethyl-4-aminomethylphenol;
N,N-dimethyl,2,6-diethyl-4-aminomethylphenol;
N,N-dimethyl,2,6-diisopropyl-4-aminomethylphenol;
N,N-dimethyl,2,6-di-sec-butyl-4-aminomethylphenol;
N,N-dimethyl,2,6-diheptyl-4-aminomethylphenol;
N,N-dimethyl,2,6-dioctyl-4-aminomethylphenol;
N,N-dimethyl,2,6-di-t-butyl-4-aminomethylphenol;
N,N-dimethyl,2-methyl-6-isopropyl-4-aminomethylphenol;
N,N-dimethyl,2-methyl-6-t-butyl-4-aminomethylphenol;
N,N-diethyl,2,6-di-t-butyl-4-aminomethylphenol;
N,N-dioctyl,2,6-di-t-butyl-4-aminomethylphenol;
N,N-dioctyl,2-ethyl-6-t-butyl-4-aminomethylphenol;
N,N-dioctyl,2,6-diheptyl-4-aminomethylphenol;
N,N-dioctyl,2-ethyl-6-methyl-4-aminomethylphenol;
N,N-dioctyl,2-t-butyl-6-heptyl-4-aminomethylphenol;
N-ethyl,N-methyl-2,6-di-t-butyl-4-aminomethylphenol;
N-octyl,N-methyl,2-methyl-6-ethyl-4-aminomethylphenol;
3,5-di-t-butyl-4-hydroxybenzylpiperidine;
3,5-di-t-butyl-4-hydroxybenzylmorpholine;
3,5-di-t-butyl-4-hydroxybenzylpyrrolidine,
and the like.

Representative examples of Group II diene reactants include:
1,3-butadiene;
2-methyl-1,3-butadiene;
2,3-dimethyl-1,3-butadiene,
2,3-diethyl-1,3-butadiene;
2,3-dipentyl-1,3-butadiene;
1,3-pentadiene;
1,3-hexadiene;
1,3-octadiene;
2,4-hexadiene;
2,4-heptadiene;
3,5-octadiene;
2-methyl-1,3-pentadiene;
2,3-dimethyl-1,3-pentadiene;
3-methyl-2,4-hexadiene;
3,4-dimethyl-2,4-hexadiene;
4-methyl-3,5-octadiene;
4,5-dimethyl-3,5-octadiene;
1-phenyl-1,3-butadiene;
2-phenyl-1,3-butadiene;
1,4-diphenyl-1,3-butadiene;
1-phenyl-1,3-pentadiene;
1-phenyl-1,3-hexadiene;
1-phenyl-1,3-heptadiene;
1-phenyl-1,3-octadiene;
1,6-diphenyl-2,4-hexadiene;
1-cyclohexyl-1,3-butadiene;
2-cyclohexyl-1,3-butadiene;
2,3-dicyclohexyl-1,3-butadiene;
and the like.

Representative examples of Group III compounds include:
methyl iodide,
octyl iodide,
methyl bromide,
octyl bromide,
methyl chloride,
octyl chloride,
isopropyl iodide,
isopropyl bromide,
sec-butyliodide,
sec-butylbromide,
3-methyliodobutane,
and the like.

Representative examples of spiroketone products which are made by the process of the present invention include:
2-methylspiro[5.5]undeca-1,4,8-trien-3-one;
2-ethylspiro[5.5]undeca-1,4,8-trien-3-one;
2-isopropylspiro[5.5]undeca-1,4,8-trien-3-one;
2-sec-butylspiro[5.5]undeca-1,4,8-trien-3-one;
2-butylspiro[5.5]undeca-1,4,8-trien-3-one;
2-heptylspiro[5.5]undeca-1,4,8-trien-3-one;
2-octylspiro[5.5]undeca-1,4,8-trien-3-one;
2,4-dimethylspiro[5.5]undeca-1,4,8-trien-3-one;
2,4-diethylspiro[5.5]undeca-1,4,8-trien-3-one;
2,4-diisopropylspiro[5.5]undeca-1,4,8-trien-3-one;
2,4-di-sec-butylspiro[5.5]undeca-1,4,8-trien-3-one;
2,4-di-t-butylspiro[5.5]undeca-1,4,8-trien-3-one;
2,4-diheptylspiro[5.5]undeca-1,4,8-trien-3-one;
2,4-dioctylspiro[5.5]undeca-1,4,8-trien-3-one;
2-methyl-4-isopropylspiro[5.5]undeca-1,4,8-trien-3-one;
2-methyl-4-t-butylspiro[5.5]undeca-1,4,8-trien-3-one;
2-ethyl-4-t-butylspiro[5.5]undeca-1,4,8-trien-3-one;
2,4-diheptylspiro[5.5]undeca-1,4,8-trien-3-one;
2-ethyl-4-methylspiro[5.5]undeca-1,4,8-trien-3-one;
2-t-butyl-4-heptylspiro[5.5]undeca-1,4,8-trien-3-one;
2-methyl-4-ethylspiro[5.5]undeca-1,4,8-trien-3-one;
2,4-di-t-butyl-8-methylspiro[5.5]undeca-1,4,8-trien-3-one;
2,4-di-t-butyl-9-methylspiro[5.5]undeca-1,4,8-trien-3-one;
2,4-di-t-butyl-8,9-dimethylspiro[5.5]undeca-1,4,8-trien-3-one;

2,4-di-t-butyl-8,9-diethylspiro[5.5]undeca-1,4,8-trien-3-one;
2,4-di-t-butyl-8,9-dipentylspiro[5.5]undeca-1,4,8-trien-3-one;
2,4-di-t-butyl-7-methylspiro[5.5]undeca-1,4,8-trien-3-one;
2,4-di-t-butyl-10-methylspiro[5.5]undeca-1,4,8-trien-3-one;
2,4-di-t-butyl-7-ethylspiro[5.5]undeca-1,4,8-trien-3-one;
2,4-di-t-butyl-10-ethylspiro[5.5]undeca-1,4,8-trien-3-one;
2,4-di-t-butyl-7-n-butylspiro[5.5]undeca-1,4,8-trien-3-one;
2,4-di-t-butyl-10-n-butylspiro[5.5]undeca-1,4,8-trien-3-one;
2,4-di-t-butyl-7,10-dimethylspiro[5.5]undeca-1,4,8-trien-3-one;
2,4-di-t-butyl-7-methyl-10-ethylspiro[5.5]undeca-1,4,8-trien-3-one;
2,4-di-t-butyl-7-ethyl-10-methylspiro[5.5]undeca-1,4,8-trien-3-one;
2,4-di-t-butyl-7,10-diethylspiro[5.5]undeca-1,4,8-trien-3-one;
2,4-di-t-butyl-7,9-dimethylspiro[5.5]undeca-1,4,8-trien-3-one;
2,4-di-t-butyl-8,10-dimethylspiro[5.5]undeca-1,4,8-trien-3-one;
2,4-di-t-butyl-7,8,9-trimethylspiro[5.5]undeca-1,4,8-trien-3-one;
2,4-di-t-butyl-8,9,10-trimethylspiro[5.5]undeca-1,4,8-trien-3-one;
2,4-di-t-butyl-7,8,10-trimethylspiro[5.5]undeca-1,4,8-trien-3-one;
2,4-di-t-butyl-7,9,10-trimethylspiro[5.5]undeca-1,4,8-trien-3-one;
2,4-di-t-butyl-7,8,9,10-tetramethylspiro[5.5]undeca-1,4,8-trien-3-one;
2,4-di-t-butyl-7,10-diethyl-8-methylspiro[5.5]undeca-1,4,8-trien-3-one;
2,4-di-t-butyl-7,10-diethyl-9-methylspiro[5.5]undeca-1,4,8-trien-3-one;
2,4-di-t-butyl-7,10-diethyl-8,9-dimethylspiro[5.5]undeca-1,4,8-trien-3-one;
2,4-di-t-butyl-7-phenylspiro[5.5]undeca-1,4,8-trien-3-one;
2,4-di-t-butyl-10-phenylspiro[5.5]undeca-1,4,8-trien-3-one;
2,4-di-t-butyl-8-phenylspiro[5.5]undeca-1,4,8-trien-3-one;
2,4-di-t-butyl-9-phenylspiro[5.5]undeca-1,4,8-trien-3-one;
2,4-di-t-butyl-7,10-diphenylspiro[5.5]undeca-1,4,8-trien-3-one;
2,4-di-t-butyl-7-benzylspiro[5.5]undeca-1,4,8-trien-3-one;
2,4-di-t-butyl-10-benzylspiro[5.5]undeca-1,4,8-trien-3-one;
2,4-di-t-butyl-7-phenyl-10-ethylspiro[5.5]undeca-1,4,8-trien-3-one;
2,4-di-t-butyl-7-ethyl-10-phenylspiro[5.5]undeca-1,4,8-trien-3-one;
2,4-di-t-butyl-7-phenyl-10-n-propylspiro[5.5]undeca-1,4,8-trien-3-one;
2,4-di-t-butyl-7-n-propyl-10-phenylspiro[5.5]-undeca-1,4,8-trien-3-one;
2,4-di-t-butyl-7-phenyl-10-n-butylspiro[5.5]undeca-1,4,8-trien-3-one;
2,4-di-t-butyl-7-n-butyl-10-phenylspiro[5.5]undeca-1,4,8-trien-3-one;
2,4-di-t-butyl-7,10-dibenzylspiro[5.5]undeca-1,4,8-trien-3-one;
2,4-di-t-butyl-7-cyclohexylspiro[5.5]undeca-1,4,8-trien-3-one;
2,4-di-t-butyl-10-cyclohexylspiro[5.5]undeca-1,4,8-trien-3-one;
2,4-di-t-butyl-8-cyclohexylspiro[5.5]undeca-1,4,8-trien-3-one;
2,4-di-t-butyl-9-cyclohexylspiro[5.5]undeca-1,4,8-trien-3-one;
2,4-di-t-butyl-8,9-dicyclohexylspiro[5.5]undeca-1,4,8-trien-3-one;
and the like.

The process of the invention is carried out by reacting the benzylamine starting material with at least one molar equivalent of diene reactant and one molar equivalent of alkyl halide although an excess of either or both the dioene or halide reactant can be used. A preferred range of diene reactant to benzylamine reactant is from about 1 to 10 moles of diene per mole of benzylamine. A preferred range of alkyl halide reactant to benzylamine reactant ranges from about 1 to 10 moles of halide per mole of benzylamine.

The reaction is advantageously conducted at an elevated temperature typically ranging from about 50° C. up to about 200° C. While lower temperatures can be used, the reaction rates are generally correspondingly lower. Temperatures above 200° C. can be used, however, at temperatures exceeding approximately 500° C., excessive decomposition of the reaction components can occur. When reaction temperatures above the boiling point of the diene reactant are used, elevated pressures must be employed to prevent volatilization of the diene reactant. Typically, pressures of from about 10 psig up to approximately 1000 psig can be used.

The reaction is normally carried out in a suitable solvent. Suitable solvents are those solvents which are inert under the reaction conditions, i.e., those solvents which do not enter into the reaction. Useful solvents which may be used include ethers such as diethyl ether, dibutyl ether, 1-ethoxyhexane, tetrahydrofuran, 1,4-dioxane, 1,3-dioxolane, diglyme and 1,2-diethoxyethane. Especially useful solvents are dipolar aprotic solvents such as dimethyl sulfoxide, N,N-dimethylformamide, N,N-dimethylacetamide, dimethyl sulfone, tetramethylene sulfone, N-methylpyrrolidinone, acetonitrile and like materials. Other solvents which are inert under the reaction conditions may be used: for example, low boiling hydrocarbons, halogenated hydrocarbons, examples of which are benzene, toluene, tetrachlorethane, the chlorinated benzenes, the chlorinated toluenes, etc., and lower alkanols having up to about 6 carbon atoms. These include methanol, ethanol, n-propanol, isopropyl alcohol, n-butanol, sec-butyl alcohol, t-butyl alcohol, n-pentanol, iso-pentyl alcohol, n-hexanol and isohexyl alcohol. A preferred solvent is ethyl acetate.

The amount of solvent used can be expressed as a volume ratio of solvent to benzylamine reactant. Suitable volume ratios of solvent to benzylamine reactant can be from about 0/1 to about 500/1 and preferably from about 1/1 to about 300/1.

The mode of addition in the process is not particularly critical. Accordingly, it is convenient to add the benzylamine reactant to a mixture of the other materials, add the diene compound to a mixture of the other materials, add the alkyl halide reactant to a mixture of the other materials, introduce all ingredients simultaneously into the reaction zone, or the like.

The process should be carried out for the time sufficient to convert substantially all of the benzylamine reactant to the corresponding 2,4-dihydrocarbylspiro[5.5]undeca-1,4,8-trien-3-one. The length of time for optimum yield will depend primarily upon the reaction temperature and the particular solvent, if any, used in the reaction. In general, excellent yields of the 2,4-dihydrocarbylspiro[5.5]undeca-1,4,8-trien-3-one are obtained in from about four to thirty hours.

Although not required, it is preferred to carry out the process in a substantially anhydrous reaction system, and accordingly, the components of the reaction system are brought together and maintained under a substantially dry, inert atmosphere. By "substantially anhydrous" is meant a reaction system wherein the total amount of water present is no more than about 5 percent by weight, based on the reaction mixture. When the amount of water in the system exceeds this, both reaction rate and yield of product decrease.

The process may readily be conducted in a batch-wise, semi-batchwise or continuous manner and in conventional equipment.

The process of the invention when run continuously can be illustrated schematically by the equation shown below. $R_1$, $R_2$, $R_3$, $R_4$, $R_5$, $R_6$, $R_7$, $R_8$ and $R_9$ are the same radicals and X represents the same halogens as described and exemplified above.

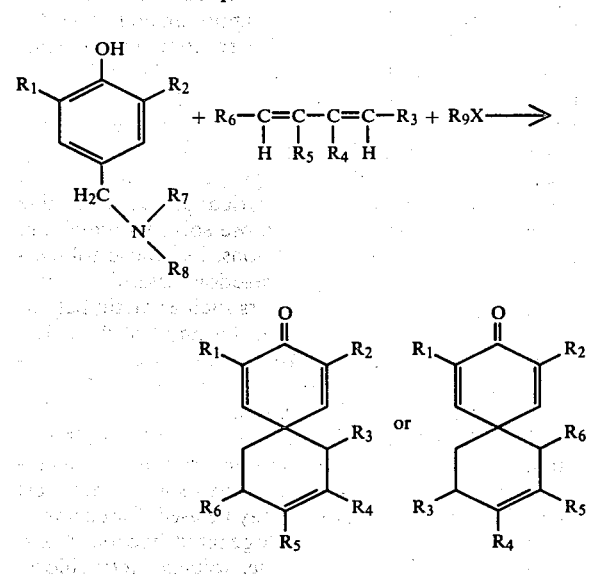

Under the reaction conditions, the benzylamine reactant is alkylated to initially yield a quaternary ammonium salt of the benzylamine reactant which subsequently eliminates a tertiary amine compound from the salt to produce a quinone methide intermediate. The quinone methide subsequently undergoes cycloaddition with the diene reactant to form the desired 2,4-dihydrocarbylspiro[5.5]undeca-1,4,8-trien-3-one product. The use of an unsymmetrical diene in the practice of the process results in the formation of structural isomers having the configurations depicted in the above schematic equation. Conversely, when a symmetrical conjugated diene reactant is used in the reaction, the formation of structural isomers is precluded. Therefore, the selection of the particular diene reactant will determine whether or not isomeric spiroketone compounds will be obtained. The 2,4-dihydrocarbylspiro[5,5]undeca-1,4-8-trien-3-one product is easily separated from the reaction mixture by such means as distillation, extraction, crystallization, and other methods obvious to those skilled in the chemical processing art.

Since the 2,4-dihydrocarbylspiro[5,5]undeca-1,4-8-trien-3-one products of the present process are believed to be novel compounds, in a still further embodiment of the present invention, there is provided, as new compositions of matter, compounds of the general formula:

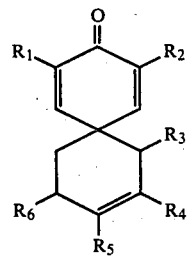

wherein $R_1$ and $R_2$ are the same or different and are hydrogen or hydrocarbyl radicals having up to at least 40 carbon atoms and $R_3$, $R_4$, $R_5$ and $R_6$ are the same or different and are hydrogen or linear or branched alkyl, aralkyl or cycloalkyl radicals having up to 8 carbon atoms each and the structural isomers thereof.

An advantage of this invention is that the 2,4-dihydrocarbylspiro[5.5]undeca-1,4,8-triene-3-one products prepared by the process of this invention are useful as intermediates in the synthesis of flame retardant compounds. Flame retardant compounds which can be used to impart flame retardancy to normally flammable organic polymers can be readily prepared by halogenating the novel spiroketone compounds of this invention with chlorine or bromine at the points of unsaturation with addition reactions or by substitution reactions for atoms or groups in the spiroketone molecules at conditions well known in the art. See, for example, Lyons, J. W. *The Chemistry and Uses of Flame Retardants*, N.Y., J. Wiley & Sons, Inc., 1970, pp. 88–107.

The normally flammable organic polymers which may be rendered flame retardant in accordance with the invention may be natural or synthetic but are preferably solid synthetic polymers, more preferably polymers of an unsaturated hydrocarbon. Exemplary of the polymers are cotton, wool, silk, paper, natural rubber, wood, paint, the high molecular weight homopolymers and copolymers of unsaturated aliphatic and aromatic hydrocarbons (e.g., ethylene, propylene, styrene, etc.), acrylic polymers (e.g., polyacrylonitrile, polymethylmethacrylate, etc.), alkyd resins, cellulose derivatives (e.g., cellulose acetate, methyl cellulose, etc.), epoxy resins, furan resins, isocyanate resins (e.g., polyurethanes), melamine resins, vinyl resins (e.g., polyvinyl acetate, polyvinyl chloride, etc.), resorcinol resins, synthetic rubbers (e.g., polyisoprene, polybutadiene, butadiene-acrylonitrile copolymers, butadiene-sytrene copolymers, butyl rubber, neoprene rubber, etc.), ABS resins, and mixtures thereof.

The organic polymer is intimately mixed with the flame retardant and any optional conventional additives, such as fillers, pigments, plasticizers, stabilizers, synergists, etc., in any suitable manner (e.g., by the use of an extruder, a two-roll mill or a Banbury mixer). The amount of flame retardant incorporated into the polymer substrate will vary, of course, depending on such variables as the specific substrate to which the flame retardant is added and other conditions such as temperature to which the combined substrate and flame retardant compositions are exposed. In general, however, compositions containing from about 1–25%, preferably 4–20% by weight of flame retardant, based on the combined weights of organic polymer and flame retardant, are contemplated by the present invention, although amounts of flame retardant above and below these ranges may be used, if desired.

Frequently, it may be desirable to include in the polymer substrate one or more of the compounds of antimony, arsenic or bismuth which are well known synergists for halogenated hydrocarbons to enhance the effectiveness of the flame retardant compounds aforediscussed. Antimony trioxide is particularly useful. When such a synergist is employed, it is usually used in an amount such as to provide a flame retardant/synergist weight ratio of about 1–4.5/1, preferably about 2/1.

It is also contemplated that chlorinated derivatives of the novel spiroketone compounds of the present invention which can be prepared by reacting chlorine with the spiroketone products of the invention by addition or substitution reactions as discussed previously can be utilized for the control of insect pests. The chlorinated compounds can be used in the form of pure compounds, as technical grade compounds or as mixtures of specific compounds. They may also be used in the form of typical insecticidal formulations such as emulsion concentrates, dispersions, wetable powders, dusts or granules. In addition, they may contain the usual adhesives, emulsifiers, wetting agents, dispersing agents, fillers and carriers. Emulsifiable concentrates are obtained by dissolving the active chlorinated spiroketone product in suitable organic solvents, for example, toluenes, xylenes, chlorobenzenes and other aromatic compounds of high boiling points, petrols or parafin oils; cyclohexanone, dimethylformamide, dimethylsulfoxide, tetrahydrofuran, dioxane, diacetonyl alcohol, ethyl acetate and isophronone.

Suitable carrier materials for solids formulations can be, in particular, mineral substances such as silicic acids and silicates such as diatomaceous earth, kaolines, alumina or talc, chalk or siliceous chalk; or formulations of these mineral substances, with additives, such as stearates, alkyl-, aryl- or alkylarylsulfonates, lignosulfonates, and the like. Moreover, there may be used further wetting agents, dispersing agents and adhesives or most different kinds of grinding auxilliaries, depending on the intended application.

While the amount of active ingredient in the formulations may vary widely, in general, from 10–90% by weight of active ingredient based on the total weight of ther formulation will be suitable for use in the practice of the invention.

Another advantage of the present invention is that the spiroketone products prepared by the process of this invention may be used as antioxidants for oxidizable organic materials when such materials are exposed to oxidative degradative conditions and are capable of stabilizing polymers normally subject to oxidative degradation when incorporated into the polymers using conventional techniques such as by addition to polymer lattices; or by addition to solid polymers on a mill or in a Banbury.

Examples of polymers which may be stabilized against oxidative degradation by the novel spiroketone compounds of the present invention include the high molecular weight homopolymers and copolymers of unsaturated aliphatic and aromatic hydrocarbons such as ethylene, propylene, styrene, etc., acrylic polymers such as polyacrylonitrile, polymethylmethacrylate, etc., vinyl resins such as polyvinyl acetate, polyvinyl chloride, etc., synthetic rubbers such as polyisoprene, polybutadiene, butadiene-acrylonitrile copolymers, butadiene-styrene copolymers, butyl rubber, neoprine rubber, etc., ABS resins, and mixtures thereof.

Further, the novel compounds of this invention are effective antioxidants in both unleaded and leaded gasolines made from a wide variety of base stocks and for engine and industrial oils which are derived from crude petroleum or produced synthetically.

Especially effective antioxidant compounds are those compounds of the general formula:

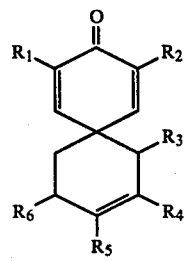

wherein $R_1$ and $R_2$ are the same or different and are hydrogen or hydrocarbyl radicals, preferably alkyl, aralkyl or cycloalkyl radicals having up to at least 40 carbon atoms, and preferably from 3 to 8 atoms, at least one of which is branched on the α-carbon atom, with the provision that at least one of $R_1$ or $R_2$ must be other than hydrogen and $R_3$, $R_4$, $R_5$ and $R_6$ are the same or different and are hydrogen or linear or branched alkyl, aralkyl or cycloalkyl radicals having up to 8 carbon atoms each and the structural isomers thereof.

Thus, in another embodiment of the present invention there is provided a liquid hydrocarbon fuel of the gasoline boiling range for spark ignition internal combustion engines normally susceptible to deterioration in the presence of oxygen containing in an amount sufficient to inhibit such deterioration, a compound of the general formula:

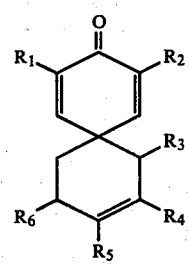

wherein $R_1$ and $R_2$ are the same or different and are hydrogen or hydrocarbyl radicals, preferably alkyl, aralkyl or cycloalkyl radicals having up to at least 40 carbon atoms, and preferably from 3 to 8 atoms, at least one of which is branched on the α-carbon atom, with the provision that at least one of $R_1$ or $R_2$ must be other than hydrogen and $R_3$, $R_4$, $R_5$ and $R_6$ are the same or different and are hydrogen or linear or branched alkyl, aralkyl or cycloalkyl radicals having up to 8 carbon atoms each and the structural isomers thereof.

A still further embodiment of the present invention is lubricating oil normally susceptible to oxidative deterioration containing a small antioxidant quantity of a compound of the general formula:

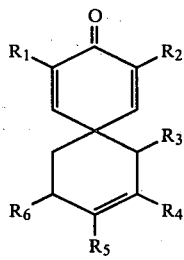

wherein $R_1$ and $R_2$ are the same or different and are hydrogen or hydrocarbyl radicals, preferably alkyl, aralkyl or cycloalkyl radicals having up to at least 40 carbon atoms, and preferably from 3 to 8 atoms, at least one of which is branched on the α-carbon atom, with the provision that at least one of $R_1$ or $R_2$ must be other than hydrogen and $R_3$, $R_4$, $R_5$ and $R_6$ are the same or different and are hydrogen or linear or branched alkyl, aralkyl or cycloalkyl radicals having up to 8 carbon atoms each and the structural isomers thereof.

The practice of this invention will still be further apparent by the following illustrative examples.

EXAMPLE 1

To a 250 mL glass reaction vessel containing an ethyl acetate (50 mLs) solution of N,N-dimethyl,2,6-di-t-butyl-4-aminomethylphenol (1.32 g; 5 mmols), there was added methyl iodide (0.31 mLs; 5 mmols) to give a colorless slurry. The vessel was sealed and 1,3-butadiene (20 mmols) was introduced into the system. The reaction mixture was heated to 100° C. and the pressure was increased from atmospheric to 45 psig. The reaction mixture was maintained at these conditions for approximately 30 hours. The reaction vessel was then allowed to cool to room temperature. After cooling, the black reaction mixture was filtered to remove ammonium iodide salt by-product. The filtrate was concentrated to afford a viscous oil which was crystallized from ethanol:water (80:20) to give 1.34 g of 2,4-di-t-butylspiro[5.5]undeca-1,4,8-trien-3-one (49% yield based on the N,N-dimethyl,2,6-di-t-butyl-4-aminomethylphenol starting reactant) as colorless crystals.

EXAMPLE 2

To a 250 mL glass reaction vessel containing an ethyl acetate (70 mLs) solution of N,N-dimethyl,2,6-dimethyl-4-aminomethylphenol (3.58 g; 20 mmols), there was added methyl iodide (20 mmols) to give a colorless slurry. The vessel was sealed and 2-methyl-1,3-butadiene (100 mmols) was introduced into the system. The reaction mixture was heated to 135° C. and the pressure was increased from atmospheric to 75 psig. The reaction mixture was maintained at these conditions for approximately 4 hours. The reaction vessel was then allowed to cool to room temperature. After cooling the black reaction mixture was filtered to remove ammonium iodide salt by-product. The filtrate was concentrated to afford a viscous oil which was purified by column chromatography (silica gel eluted with heptane) to give 1.1 g of 2,4,8-trimethylspiro[5.5]undeca-1,4,8-trien-3-one and 2,4,9-trimethylspiro[5.5]undeca-1,4,8-trien-3-one (33% yield based on N,N-dimethyl,2,6-dimethyl-4-aminomethylphenol starting reactant).

EXAMPLE 3

To a 250 mL glass reaction vessel containing an ethyl acetate (120 mLs) solution of N,N-dimethyl,2,6-dimethyl-4-aminomethylphenol (7.16 g; 40 mmols), there was added methyl iodide (40 mmols) to give a colorless slurry. The vessel was sealed and 1,3-butadiene (200 mmols) was introduced into the vessel. The reaction mixture was heated to 130° C. and the pressure was increased from atmospheric to 70 psig. The reaction mixture was maintained at these conditions for approximately 5 hours. The reaction vessel was cooled to room temperature. After cooling, the reaction mixture was filtered to remove ammonium iodide salt by-product. The filtrate was concentrated to afford a viscous oil which was purified by column chromatography (ethyl acetate/silica gel) to give 6.02 g of 2,4-dimethylspiro[5.5]undeca-1,4,8-trien-3-one (76% yield by vapor phase chromatography).

EXAMPLE 4

To a 250 mL glass reaction vessel containing an ethyl acetate (120 mLs) solution of N,N-dimethyl,2,6-dimethyl-4-aminomethylphenol (3.58 g; 20 mmols), there was added methyl iodide (20 mmols) to give a colorless slurry. The reaction vessel was sealed and 1,3-butadiene (100 mmols) was introduced into the system. The reaction mixture was heated to 120° C. and the pressure was increased from atmospheric up to 70 psig. The reaction mixture was maintained at these conditions for approximately 16 hours. The reaction vessel was then cooled to room temperature. After cooling, the reaction mixture was filtered to remove ammonium iodide salt by-product. The filtrate was concentrated to afford a viscous oil which was crystallized from ethanol to give 3.3 g of 2,4-dimethylspiro[5.5]undeca-1,4,8-trien-3-one (84% yield by vapor phase chromatography).

EXAMPLE 5

To a 250 mL glass reaction vessel there was added a dimethylformamide (10 mLs) solution of N,N-dimethyl,2,6-di-t-butyl-4-aminomethylphenol (2.63 g; 10 mmols). The vessel was sealed and 1,3-butadiene (40 mmols) was introduced into the system. The reaction mixture was then heated to 110° C. and the pressure was increased from atmospheric up to approximately 50 psig. The reaction was maintained at these conditions for approximately 48 hours. The reaction vessel was then cooled to room temperature. After cooling, the reaction mixture was filtered to remove ammonium iodide salt by-product. The filtrate was concentrated to afford a viscous oil crystallized with ethanol:water (60:40) to give 0.11 g of 2,4-di-t-butylspiro[5.5]undeca-1,4,8-trien-3-one (49% yield based on N,N-dimethyl,2,6-di-t-butyl-4-aminomethylphenol starting reactant).

Having disclosed the process of the present invention, one skilled in the art can readily envision various modifications and changes which are nevertheless within the scope of the invention. Therefore, it is desired that the process of this invention be limited only by the lawful scope of the appended claims.

I claim:

1. A process for the preparation of 2,4-dihydrocarbyl-spiro[5.5]undeca-1,4,8-trien-3-one compounds which comprises reacting an N,N-dihydrocarbyl,2,6-dihydrocarbyl-4-aminomethylphenol with a conjugated diene and an alkyl halide in a liquid solvent medium.

2. A process for the preparation of 2,4-dihydrocarbyl-spiro[5.5]undeca-1,4,8-trien-3-one compounds having the general structural formula:

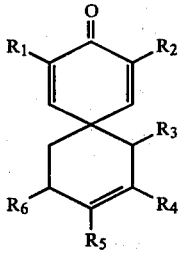

and the structural isomers thereof, which comprises reacting an N,N-dihydrocarbyl,2,6-dihydrocarbyl-4-aminomethylphenol of the general structural formula:

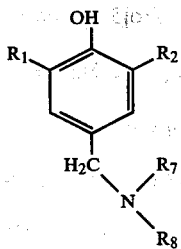

with a conjugated diene of the general structural formula:

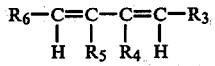 (II)

and an alkyl halide of the general formula:

in the presence of a liquid solvent wherein $R_1$ and $R_2$ are the same or different and are hydrogen or hydrocarbyl radicals having up to at least 40 carbon atoms and $R_3$, $R_4$, $R_5$ and $R_6$ are the same or different and are hydrogen or linear or branched alkyl, aralkyl, or cycloalkyl radicals having up to 8 carbon atoms each; $R_7$ and $R_8$ are the same or different and are hydrogen or hydrocarbyl radicals having up to at least 20 carbon atoms; $R_9$ is a linear or branched monovalent alkyl radical having up to at least 20 carbon atoms and X is chlorine, bromine or iodine.

3. The process of claim 2 wherein compounds having the general structural formula (I) are selected from the group consisting of:
2,6-di-t-butyl-4-aminomethylphenol;
N-methyl,2,6-di-t-butyl-4-aminomethylphenol;
N,N-dimethyl,2-methyl-4-aminomethylphenol;
N,N-dimethyl,2-ethyl-4-aminomethylphenol;
N,N-dimethyl,2-isopropyl-4-aminomethylphenol;
N,N-dimethyl,2-sec-butyl-4-aminomethylphenol;
N,N-dimethyl,2-butyl-4-aminomethylphenol;
N,N-dimethyl,2-heptyl-4-aminomethylphenol;
N,N-dimethyl,2-octyl-4-aminomethylphenol;
N,N-dimethyl,2,6-dimethyl-4-aminomethylphenol;
N,N-dimethyl,2,6-diethyl-4-aminomethylphenol;
N,N-dimethyl,2,6-diisopropyl-4-aminomethylphenol;
N,N-dimethyl,2,6-di-sec-butyl-4-aminomethylphenol;
N,N-dimethyl,2,6-diheptyl-4-aminomethylphenol;
N,N-dimethyl,2,6-dioctyl-4-aminomethylphenol;
N,N-dimethyl,2,6-di-t-butyl-4-aminomethylphenol;
N,N-dimethyl,2-methyl-6-isopropyl-4-aminomethylphenol;
N,N-dimethyl,2-methyl-6-t-butyl-4-aminomethylphenol;
N,N-diethyl,2,6-di-t-butyl-4-aminomethylphenol;
N,N-dioctyl,2,6-di-t-butyl-4-aminomethylphenol;
N,N-dioctyl,2-ethyl-6-t-butyl-4-aminomethylphenol;
N,N-dioctyl,2,6-diheptyl-4-aminomethylphenol;
N,N-dioctyl,2-ethyl-6-methyl-4-aminomethylphenol;
N,N-dioctyl,2-t-butyl-6-heptyl-4-aminomethylphenol;
N-ethyl,N-methyl,2,6-di-t-butyl-4-aminomethylphenol;
N-octyl,N-methyl,2-methyl-6-ethyl-4-aminomethylphenol;
3,5-di-t-butyl-4-hydroxybenzylpiperidine;
3,5-di-t-butyl-4-hydroxybenzylmorpholine; and
3,5-di-t-butyl-4-hydroxybenzylpyrrolidine.

4. The process of claim 2 wherein compounds having the general structural formula (II) are selected from the group consisting of:
1,3-butadiene;
2-methyl-1,3-butadiene;
2,3-dimethyl-1,3-butadiene;
2,3-diethyl-1,3-butadiene;
2,3-dipentyl-1,3-butadiene;
1,3-pentadiene;
1,3-hexadiene;
1,3-octadiene;
2,4-hexadiene;
2,4-heptadiene;
3,5-octadiene;
2-methyl-1,3-pentadiene;
2,3-dimethyl-1,3-pentadiene;
3-methyl-2,4-hexadiene;
3,4-dimethyl-2,4-hexadiene;
4-methyl-3,5-octadiene;
4,5-dimethyl-3,5-octadiene;
1-phenyl-1,3-butadiene;
2-phenyl-1,3-butadiene;
1,4-diphenyl-1,3-butadiene;
1-phenyl-1,3-pentadiene;
1-phenyl-1,3-hexadiene;
1-phenyl-1,3-heptadiene;
1-phenyl-1,3-octadiene;
1,6-diphenyl-2,4-hexadiene;
1-cyclohexyl-1,3-butadiene;
2-cyclohexyl-1,3-butadiene; and
2,3-dicyclohexyl-1,3-butadiene.

5. The process of claim 2 wherein said alkyl halide is selected from the group consisting of:
methyl iodide,
octyl iodide,
methyl bromide,
octyl bromide,
methyl chloride,
octyl chloride,
isopropyl iodide,
isopropyl bromide, sec-butyliodide,
sec-butylbromide, and
3-methyliodobutane.

6. The process of claim 2 wherein the compound produced is selected from the group consisting of:
2-methylspiro[5.5]undeca-1,4,8-trien-3-one;
2-ethylspiro[5.5]undeca-1,4,8-trien-3-one;
2-isopropylspiro[5.5]undeca-1,4,8-trien-3-one;
2-sec-butylspiro[5.5]undeca-1,4,8-trien-3-one;
2-butylspiro[5.5]undeca-1,4,8-trien-3-one;
2-heptylspiro[5.5]undeca-1,4,8-trien-3-one;
2-octylspiro[5.5]undeca-1,4,8-trien-3-one;
2,4-dimethylspiro[5.5]undeca-1,4,8-trien-3-one;
2,4-diethylspiro[5.5]undeca-1,4,8-trien-3-one;
2,4-diisopropylspiro[5.5]undeca-1,4,8-trien-3-one;
2,4-di-sec-butylspiro[5.5]undeca-1,4,8-trien-3-one;
2,4-di-t-butylspiro[5.5]undeca-1,4,8-trien-3-one;
2,4-diheptylspiro[5.5]undeca-1,4,8-trien-3-one;
2,4-dioctylspiro[5.5]undeca-1,4,8-trien-3-one;
2-methyl-4-isopropylspiro[5.5]undeca-1,4,8-trien-3-one;
2-methyl-4-t-butylspiro[5.5]undeca-1,4,8-trien-3-one;
2-ethyl-4-t-butylspiro[5.5]undeca-1,4,8-trien-3-one;
2,4-diheptylspiro[5.5]undeca-1,4,8-trien-3-one;
2-ethyl-4-methylspiro[5.5]undeca-1,4,8-trien-3-one;
2-t-butyl-4-heptylspiro[5.5]undeca-1,4,8-trien-3-one;
2-methyl-4-ethylspiro[5.5]undeca-1,4,8-trien-3-one;
2,4-di-t-butyl-8-methylspiro[5.5]undeca-1,4,8-trien-3-one;
2,4-di-t-butyl-9-methylspiro[5.5]undeca-1,4,8-trien-3-one;
2,4-di-t-butyl-8,9-dimethylspiro[5.5]undeca-1,4,8-trien-3-one;
2,4-di-t-butyl-8,9-diethylspiro[5.5]undeca-1,4,8-trien-3-one;
2,4-di-t-butyl-8,9-dipentylspiro[5.5]undeca-1,4,8-trien-3-one;
2,4-di-t-butyl-7-methylspiro[5.5]undeca-1,4,8-trien-3-one;
2,4-di-t-butyl-10-methylspiro[5.5]undeca-1,4,8-trien-3-one;
2,4-di-t-butyl-7-ethylspiro[5.5]undeca-1,4,8-trien-3-one;
2,4-di-t-butyl-10-ethylspiro[5.5]undeca-1,4,8-trien-3-one;
2,4-di-t-butyl-7-n-pentylspiro[5.5]undeca-1,4,8-trien-3-one;
2,4-di-t-butyl-10-n-pentylspiro[5.5]undeca-1,4,8-trien-3-one;
2,4-di-t-butyl-7,10-dimethylspiro[5.5]undeca-1,4,8-trien-3-one;
2,4-di-t-butyl-7-methyl-10-ethylspiro[5.5]undeca-1,4,8-trien-3-one;
2,4-di-t-butyl-7-ethyl-10-methylspiro[5.5]undeca-1,4,8-trien-3-one;
2,4-di-t-butyl-7,10-diethylspiro[5.5]undeca-1,4,8-trien-3-one;
2,4-di-t-butyl-7,9-dimethylspiro[5.5]undeca-1,4,8-trien-3-one;
2,4-di-t-butyl-8,10-dimethylspiro[5.5]undeca-1,4,8-trien-3-one;
2,4-di-t-butyl-7,8,9-trimethylspiro[5.5]undeca-1,4,8-trien-3-one;
2,4-di-t-butyl-8,9,10-trimethylspiro[5.5]undeca-1,4,8-trien-3-one;
2,4-di-t-butyl-7,8,10-trimethylspiro[5.5]undeca-1,4,8-trien-3-one;
2,4-di-t-butyl-7,9,10-trimethylspiro[5.5]undeca-1,4,8-trien-3-one;
2,4-di-t-butyl-7,8,9,10-tetramethylspiro[5.5]undeca-1,4,8-trien-3-one;
2,4-di-t-butyl-7,10-diethyl-8-methylspiro[5.5]undeca-1,4,8-trien-3-one;
2,4-di-t-butyl-7,10-diethyl-9-methylspiro[5.5]undeca-1,4,8-trien-3-one;
2,4-di-t-butyl-7,10-diethyl-8,9-dimethylspiro[5.5]undeca-1,4,8-trien-3-one;
2,4-di-t-butyl-7-phenylspiro[5.5]undeca-1,4,8-trien-3-one;
2,4-di-t-butyl-10-phenylspiro[5.5]undeca-1,4,8-trien-3-one;
2,4-di-t-butyl-8-phenylspiro[5.5]undeca-1,4,8-trien-3-one;
2,4-di-t-butyl-9-phenylspiro[5.5]undeca-1,4,8-trien-3-one;
2,4-di-t-butyl-7,10-diphenylspiro[5.5]undeca-1,4,8-trien-3-one;
2,4-di-t-butyl-7-benzylspiro[5.5]undeca-1,4,8-trien-3-one;
2,4-di-t-butyl-10-benzylspiro[5.5]undeca-1,4,8-trien-3-one;
2,4-di-t-butyl-7-phenyl-10-ethylspiro[5.5]undeca-1,4,8-trien-3-one;
2,4-di-t-butyl-7-ethyl-10-phenylspiro[5.5]undeca-1,4,8-trien-3-one;
2,4-di-t-butyl-7-phenyl-10-n-propylspiro[5.5]undeca-1,4,8-trien-3-one;
2,4-di-t-butyl-7-n-propyl-10-phenylspiro[5.5]undeca-1,4,8-trien-3-one;
2,4-di-t-butyl-7-phenyl-10-n-butylspiro[5.5]undeca-1,4,8-trien-3-one;
2,4-di-t-butyl-7-n-butyl-10-phenylspiro[5.5]undeca-1,4,8-trien-3-one;
2,4-di-t-butyl-7,10-dibenzylspiro[5.5]undeca-1,4,8-trien-3-one;
2,4-di-t-butyl-7-cyclohexylspiro[5.5]undeca-1,4,8-trien-3-one;
2,4-di-t-butyl-10-cyclohexylspiro[5.5]undeca-1,4,8-trien-3-one;
2,4-di-t-butyl-8-cyclohexylspiro[5.5]undeca-1,4,8-trien-3-one;
2,4-di-t-butyl-9-cyclohexylspiro[5.5]undeca-1,4,8-trien-3-one; and
2,4-di-t-butyl-8,9-dicyclohexylspiro[5.5]undeca-1,4,8-trien-3-one.

7. The process of claim 2 wherein the molar ratio of diene reactant to benzylamine reactant is from about 1–10 moles of diene per mole of benzylamine.

8. The process of claim 2 wherein the molar ratio of alkyl halide reactant to benzylamine reactant is from about 1–10 moles of alkyl halide per mole of benzylamine.

9. The process of claim 2 wherein said reaction is conducted at elevated temperature.

10. The process of claim 9 wherein said reaction is carried out at a temperature of from about 50° C. to about 500° C.

11. The process of claim 2 wherein said reaction is carried out under pressure in the range of atmospheric to about 1000 psig.

12. The process of claim 2 wherein said reaction is carried out at a temperature in the range of about 50° C. to about 200° C. and under pressure ranging from atmospheric up to about 1000 psig.

13. The process of claim 2 wherein said reaction is carried out in the presence of a solvent which is inert under the reaction conditions.

14. The process of claim 13 wherein the said solvent is an aprotic solvent.

15. The process of claim 13 wherein said aprotic solvent is a dipolar aprotic solvent.

16. The process of claim 15 wherein said dipolar aprotic solvent is selected from dimethyl sulfoxide; N,N-dimethylformamide; N,N-dimethylacetamide; dimethyl sulfone; tetramethylene sulfone; N-methylpyrrolidinone and acetonitrile.

17. The process of claim 13 wherein said solvent is selected from the group consisting of low boiling hydrocarbons, halogenated hydrocarbons, and lower alkanols having from about 1 to about 6 carbon atoms.

18. The process of claim 13 wherein the said solvent is ethyl acetate.

19. The process of claim 13 wherein the volume ratio of solvent to benzylamine reactant is from about 0/1 to about 500/1.

20. The process of claim 2 wherein the reaction is carried out under a substantially dry inert atmosphere.

* * * * *